(12) United States Patent
Biedermann et al.

(10) Patent No.: US 8,834,570 B2
(45) Date of Patent: Sep. 16, 2014

(54) FIXATION DEVICE FOR BONES

(75) Inventors: Lutz Biedermann, Villingen (DE); Wilfried Matthis, Weisweil (DE); Othmar Schwarzenbach, Steffisburg (CH); Martin Pabst, Donaueschingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/613,584

(22) Filed: Sep. 13, 2012

(65) Prior Publication Data

US 2013/0066428 A1 Mar. 14, 2013

Related U.S. Application Data

(63) Continuation of application No. 12/180,462, filed on Jul. 25, 2008.

(60) Provisional application No. 60/952,208, filed on Jul. 26, 2007.

(30) Foreign Application Priority Data

Jul. 26, 2007 (EP) .................................... 07014710

(51) Int. Cl.
*A61F 2/44* (2006.01)
(52) U.S. Cl.
USPC ...................................... 623/17.16
(58) Field of Classification Search
USPC ........................................... 623/17.11–17.16
See application file for complete search history.

(56) References Cited

U.S. PATENT DOCUMENTS 6,558,423 B1 5/2003 Michelson
2003/0181981 A1 9/2003 Lemaire
(Continued)

FOREIGN PATENT DOCUMENTS

EP 0 179 695 A1 4/1986
EP 1 280 481 B1 2/2003
(Continued)

OTHER PUBLICATIONS

European Search Report dated Feb. 29, 2008 for EPO Application No. EP 07014710.3, European Search Report mailed Mar. 10, 2008, Biedermann Motech GmbH (7 pages).

(Continued)

*Primary Examiner* — Sameh Boles
(74) *Attorney, Agent, or Firm* — Christie, Parker & Hale, LLP

(57) ABSTRACT

A fixation device for bones includes a member which has at least one bore for receiving a bone screw, wherein the at least one bore comprises a first internal thread portion. The bone screw has a first shaft section provided with a first external thread portion arranged to cooperate with the internal thread portion of the at least one bore, and a head section having a diameter larger than that of the shaft section to provide a catch arranged to engage with a stop formed in the bore. The bone screw further has a second shaft section which includes a clearance groove extending between the catch of the head section and the external thread of the first shaft section. The clearance groove allows disengagement of the two thread portions, such that the bone screw is prevented from being unscrewed off the bore when it is loosened within the adjacent bone.

21 Claims, 8 Drawing Sheets

(56) References Cited

U.S. PATENT DOCUMENTS

| | | |
|---|---|---|
| 2003/0208275 A1 | 11/2003 | Michelson |
| 2004/0172130 A1 | 9/2004 | Nakahara et al. |
| 2005/0090826 A1 | 4/2005 | Keller |
| 2006/0069442 A1* | 3/2006 | Michelson ................. 623/17.15 |
| 2006/0085071 A1 | 4/2006 | Lechmann et al. |
| 2007/0219635 A1 | 9/2007 | Mathieu et al. |
| 2008/0119894 A1 | 5/2008 | Ehrhardt et al. |

FOREIGN PATENT DOCUMENTS

| | | |
|---|---|---|
| FR | 2 727 003 | 5/1996 |
| JP | 09-000539 | 1/1997 |
| JP | 2008-512147 A | 4/2008 |
| TW | 570114 | 1/2004 |
| WO | WO 01/56513 A1 | 8/2001 |
| WO | WO 2004/064655 A1 | 8/2004 |
| WO | WO 2006/029274 A1 | 3/2006 |
| WO | WO 2006/072379 A1 | 7/2006 |

OTHER PUBLICATIONS

Translation of Taiwanese Office action for parallel TW Application, dated Mar. 9, 2013, 4 pages.

* cited by examiner

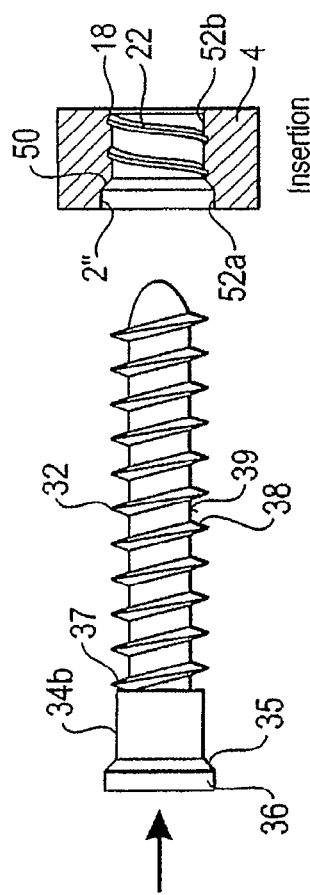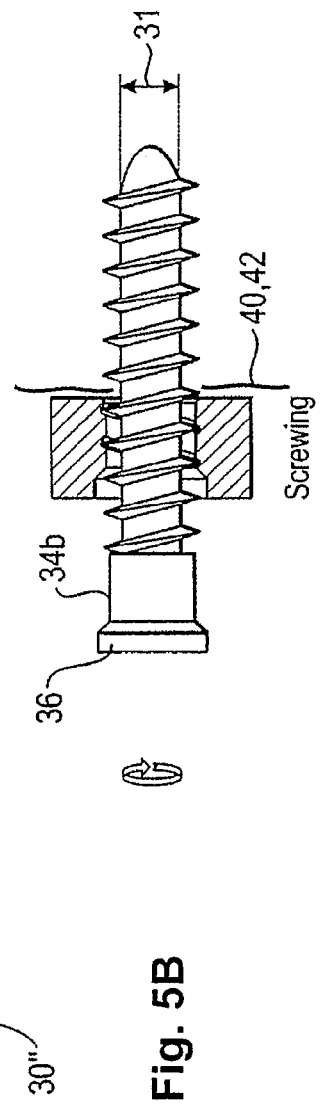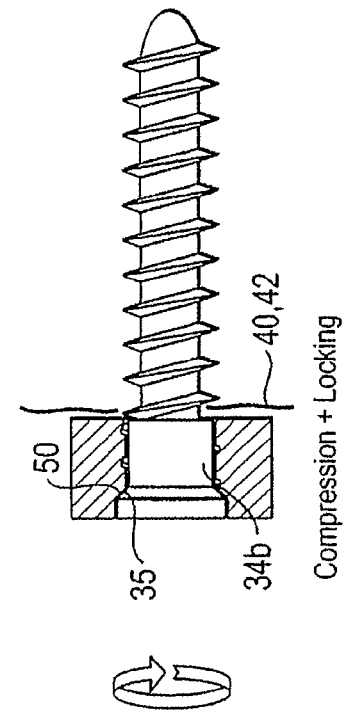
Fig. 5A
Fig. 5B
Fig. 5C

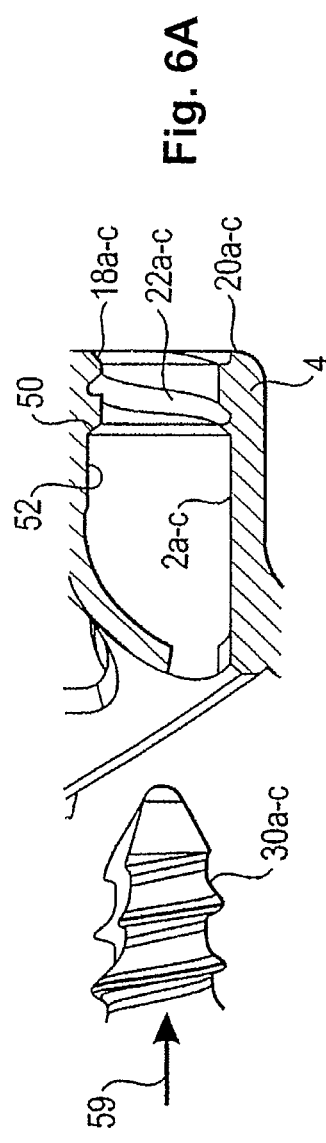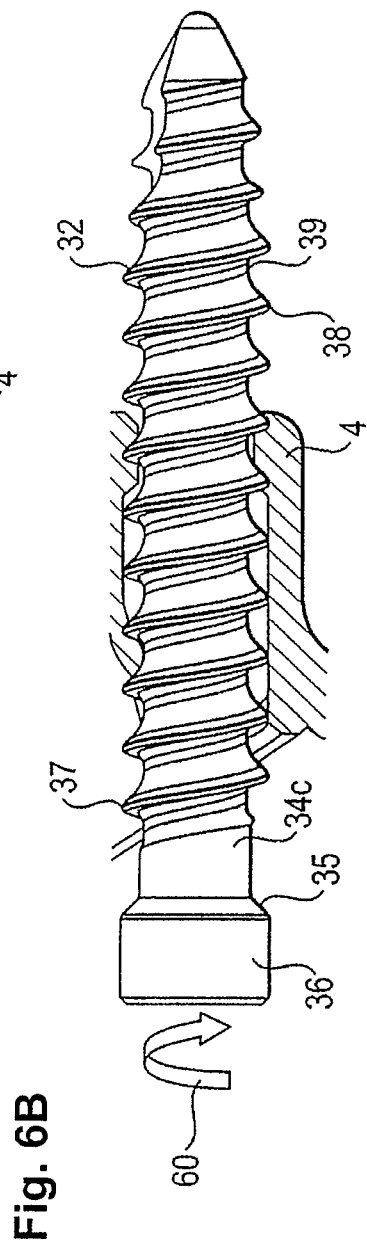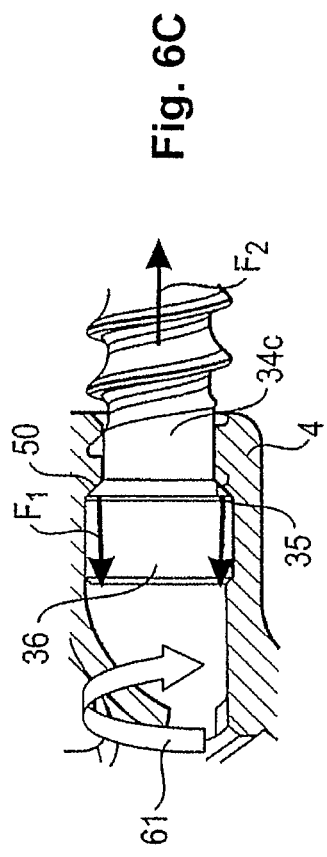

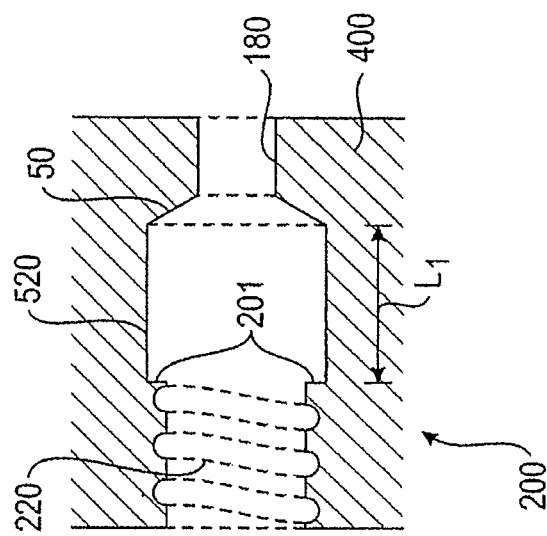
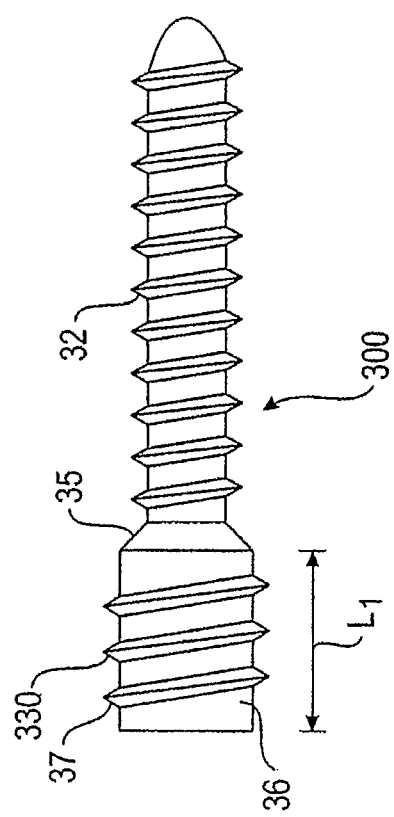
Fig. 9

FIXATION DEVICE FOR BONES

RELATED APPLICATION(S)

This application is a continuation of U.S. patent application Ser. No. 12/180,462, filed Jul. 25, 2008, which claims the benefit of U.S. Provisional Patent Application Ser. No. 60/952,208, filed Jul. 26, 2007, the contents of which are hereby incorporated by reference in their entirety, and claims priority from European Patent Application EP 07014710.3, filed Jul. 26, 2007, the contents of which are hereby incorporated by reference in their entirety.

BACKGROUND

The present application relates to a fixation device used to provide a rigid or flexible connection between bones of the human body.

Document US 2006/0085071 A1 discloses an intervertebral implant device including a body with an upper side, an under side and a front surface, in which four bore holes suited to accommodate respective bone screws are formed. The body may be formed of body-compatible plastic material. To provide rigidity and strength to the device, a small front plate made from a metallic material such as titanium or titanium alloy is attached to the front surface. Four bore holes corresponding in position to the respective bore holes of the plastic body are formed in the front plate. The bone screws may each be inserted through the bore holes of the front plate and then also extend through the bore holes of the plastic body.

The bore holes of the front plate are provided with internal threads. These internal threads correspond to external threads provided on the respective heads of the bone screws. In order to enable fixation and compression, the threaded heads are conically shaped, thereby tapering towards the shaft sections of the bone screws.

With regard to such a construction, a problem may arise that the screws may loosen and by application of external forces exerted on the vertebral bodies may slowly be screwed out, which may result in severe damage to adjacent blood vessels, and loosening of the whole implant. For this reason, US 2006/0085071 A1 further proposes to attach a securing plate to the front plate. The securing plate covers respective openings of the bore holes in the front plate and thus secures the bone screws inserted therein. As a consequence, the bone screws cannot be screwed out or fall out.

The number of parts used to implement the above described intervertebral implant device is large and the dimensions of the device may become disadvantageously large. Further, an additional screwing step has to be applied by the surgeon in order to secure the bone screws against falling out.

Document EP 1 280 481 A1 shows an intersomatic implant device comprising a cage which is composed of a sidewall. However, the holes or bores provided in the sidewall of the cage are not shown to accommodate bone screws to be inserted therein.

Based on the foregoing, there is a need to provide an improved intervertebral implant device, which simplifies handling of inserting the device between two vertebral bodies, which increases its stability against external forces once the device has been installed, which also provides an efficient downsizing of the components used and/or which protects the bone screws against being screwed out or falling out in case these are loosened.

SUMMARY

In accordance with aspects of the disclosure, an intervertebral implant device includes a device body having an upper face and a lower face for engaging with an end plate of an upper and a lower vertebral body, respectively, a side wall and at least one bore, which is formed in the side wall for receiving a bone screw as a fixation element to be inserted into vertebral body.

The bone screw typically has a shaft section with an external thread portion arranged to be anchored in the adjacent vertical body, and a head section which has a diameter larger than that of the shaft section to provide a catch arranged to engage with a stop formed in the bore of the device body.

The fixation device of the disclosure is arranged to provide a mechanism, which may hold a bone screw as a fixation element in place, which is to be inserted into an adjacent bone such as a vertebral body, even if it is loosened. For this purpose, the shaft of the bone screw has two sections: one section that is provided with the external thread portion and another section that is provided with a clearance groove.

The external thread portion may engage with the internal thread portion of a bore provided in the device body. The shaft section which includes the clearance portion extends between a head section of the bone screw and the shaft section including the external thread portion.

Hence, the bone screw may first be screwed into the internal thread portion of the bore using its external thread portion. Then upon further screwing-in of the bone screw, owing to the clearance groove, the external thread portion disengages from the internal thread portion once the entire length in longitudinal direction of the internal thread in the bore of the device body is opposed by the clearance groove.

However, it becomes further possible to continue rotation of the fixation element by, e.g., an angle of about 90 to about 270 degrees in order to separate the orientation of the thread runout of the external thread of the bone screw with respect to the thread inlet of the internal thread portion of the bore. Thus, even if the bone screw fixed in the bone, e.g., the vertebral body, is loosened with time, the helical projection part of external thread at the position of the thread runout abuts with an end face surrounding the opening of the bore due to this misorientation by, e.g., 90-270 degrees. As a result, the device body urges the bone screw to be held in place within the bone, or vertebral body respectively, in this instance.

According to an alternative but similar aspect of the invention, the bone screw is provided with a second external thread portion at the head section. This second thread portion cooperates with the internal thread portion, while the first external thread portion, i.e., the bone thread, cooperates with the bone material. A cylindrical guiding portion is formed within the bore adjacent to the internal thread portion in order to receive the head section when the second thread disengages from the internal thread portion in the bore.

The principles of abutment of the helical projection at the thread runout of second thread are the same as in the first aspect. I.e., after disengaging from the second external thread portion, the projection abuts on a respective end face inside the bore in case of a misorientation of the thread runout by for example 90-270 degrees with regard to the thread inlet of the internal thread portion. Hence, the same degree of protection against fall-out of the bone screw may be achieved as in the first aspect.

The disclosed fixation device includes a member, which is to be fixed to one or more adjacent bones, and the bone screw as the fixation element. In one embodiment this member may be embodied as a cage employed for connecting adjacent vertebral bodies.

However, the device is not limited to applications regarding the replacement of intervertebral discs by means of such cages. Rather, according to other embodiments the member may have plate-like, sleeve-like or any other suitable shapes depending on the application, in order to fix or stabilize bones of the spinal column and other areas of the remainder skeleton.

In accordance with aspects of the disclosure, the disclosed fixation devices include plates for fixing the cervical spine or plates for laterally fixing the thoracolumbar vertebrae using bone screws.

Further features and advantages of the present fixation device will become apparent and will be best understood by reference of the following detailed description taken in conjunction with the accompanying drawings.

BRIEF DESCRIPTION OF THE DRAWINGS

FIGS. 5A-C show in a schematic representation in three sectional views steps of inserting a fixation element having a clearance groove into a device body according to a third embodiment.

FIGS. 6A-C show in a schematic representation in three sectional views steps of inserting a fixation element having a clearance groove into a device body according to a first embodiment.

FIG. 9 shows a schematic illustration of an alternative embodiment of the invention.

DETAILED DESCRIPTION OF THE INVENTION

Figure 1:
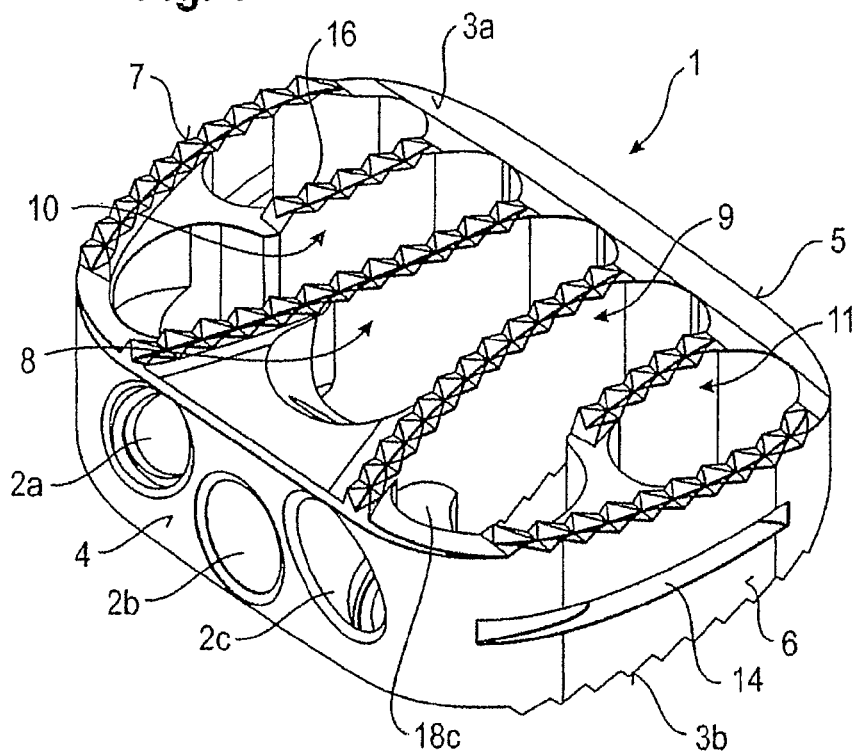
FIG. 1 shows a perspective exploded view of an intervertebral implant device according to a first embodiment.
Figure 2:
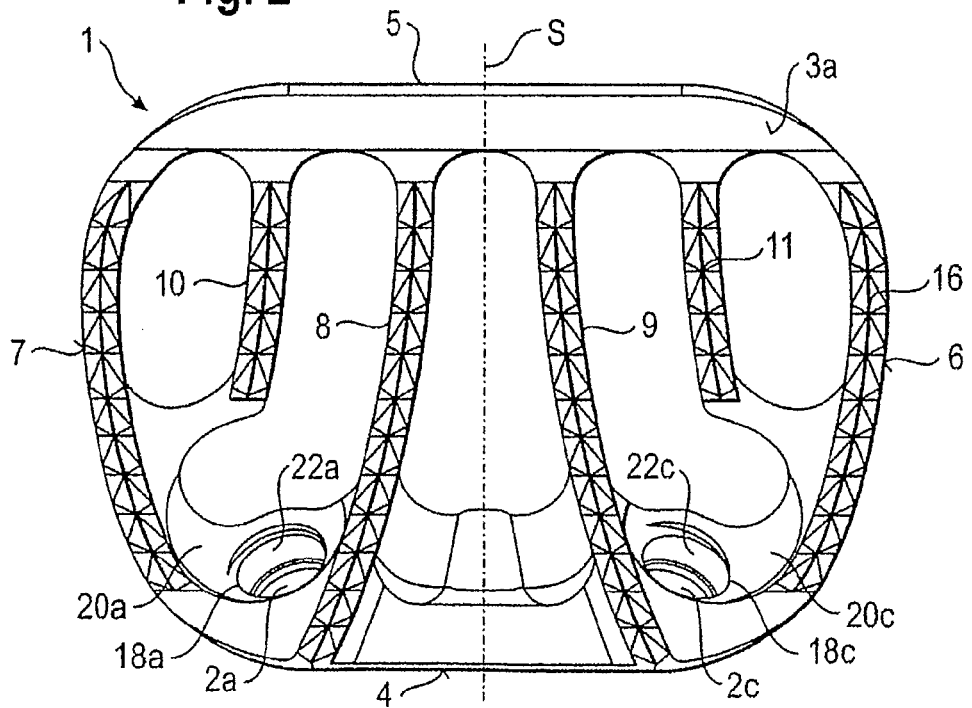
FIG. 2 shows a plan view of the device according to FIG. 1.

FIG. 1 shows in a perspective exploded view a first embodiment of a fixation device according to the present disclosure, which in this instance is a intervertebral implant device 100. FIG. 2 shows a plan view thereof. The device 100 includes a device body 1, which has the form of a cage. The cage is made of a biocompatible material such as titanium, a titanium alloy or PEEK (polyetheretherketones) and is provided with a substantially vertical sidewall enclosing one or more inner hollow spaces. The spaces are open toward an upper and a lower face 3a, 3b, respectively, of the cage 1.

The sidewall of the cage 1 is composed of a front wall 4, a back wall 5, a right side wall 6 and a left side wall 7, which are integrally formed, such that the right and left side wall connect the front and back walls with each other. The front wall 4 represents an anterior wall and the back wall 5 represents a posterior wall of the cage 1.

The rigidity of the cage 1 is further stabilized by two inner walls 8, 9 which extend in arc-shape from the back wall 5 towards the front wall 4. Both inner walls are symmetric with respect to the sagittal plane S.

There are two further inner walls 10, 11, which extend in arc-shape from the back wall towards the right and left side walls 6, 7, respectively. Similar to inner walls 8, 9, both walls 10, 11 are symmetric with regard to the sagittal plane. Each of the walls 8 to 11 has an arc-shape that is concave towards the sagittal plane, whereas the left and right side walls 6, 7 are convex thereto. This arrangement of side walls and inner walls has been found to provide an optimum load transfer at the cage-bone interface.

The five spaces defined by the side walls and inner walls are designed to be filled with bone graft material. Further, small teeth 16 are provided on the upper and lower edges of each of the walls, i.e., on the upper face 3a and lower face 3b of the cage 1, in order to facilitate a penetration into the end plates of the adjacent vertebral bodies 40, 42. The shape of the series of small teeth directly corresponds to the shape of the walls and is further optimized to anatomically fit to the adjacent vertebral bodies, i.e., good distribution of stress and torsion stability.

The cage 1 is also provided with three bores 2a, 2b, 2c each for receiving or accommodating a bone screw. The bores 2a-c are located on the front wall 4 of the cage 1, wherein one center bore 2b is inclined downward and two side bores 2a, 2c are inclined upwards. The reverse case may be arranged as well, i.e., the center bore 2b is inclined upwards and the two side bores 2a, 2c are inclined downwards. As can be seen from the top view of FIG. 2, the bores 2a, 2c have each an opening 18a, 18c respectively towards the upper face 3a of the cage 1. Due to the specific shape and arrangement of the inner walls 8 to 11, each of the three bores also opens (under respective inclinations with regard to the transversal plane) toward its own distinct inner space confined by these walls 8 to 11.

For cages intended to replace intervertebral disks, inclination angles for the bores 2a-c of 45°±20° may typically be arranged. For cages intended to function as fixation plates, inclination angles of about 90°±30° can typically be employed. However, the disclosure shall not be limited to the specific values or ranges indicated above.

The openings 22a and 22c of the bores are provided in respective end faces 20a, 20c which form part of inclined inner surfaces of the front wall 4 towards the inner spaces of the cage 1. The end faces 20a, 20c are oriented substantially perpendicular to respective longitudinal axes of the bores 2a-c. As will be detailed below, the end faces form an abutment area for projecting parts of thread runouts towards a clearance groove formed on the bone screws 30a to 30c.

Figure 3A:
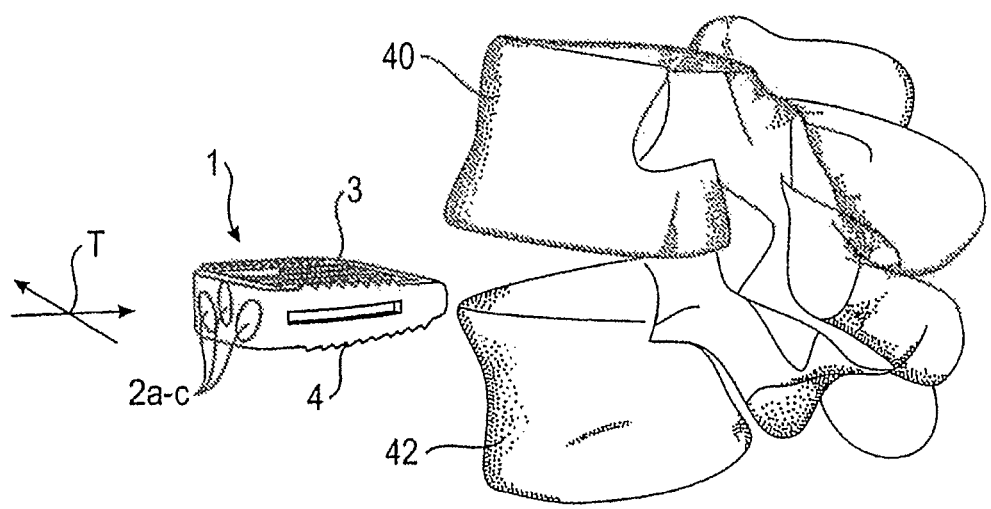
FIG. 3 shows a schematic illustration of an insertion process for the device according to FIG. 1 between two vertebral bodies.
Figure 3B:
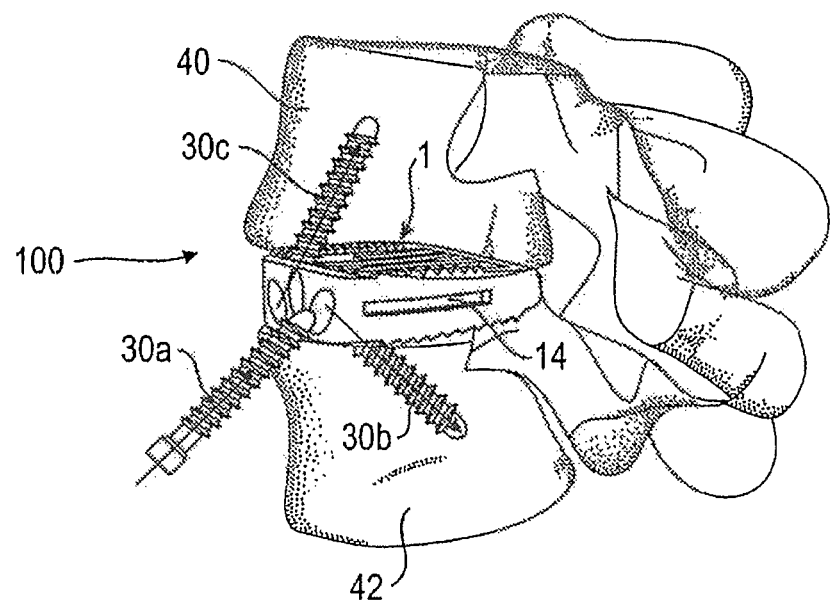

FIGS. 3A and 3B illustrate the insertion of the cage 1 between two adjacent vertebral bodies 40, 42. For this purpose a holding slot 14 is provided on either side of the cage 1, i.e., within the right side wall 6 and the left side wall 7. The holding slot 14 is elongated and extends in the transversal plane T of the cage 1. The slot allows engagement by a holding instrument which facilitates insertion of the cage 1. In this embodiment the cage 1 represents an anterior lumbar interbody fusion cage (ALIF-cage), wherein the cage is to be introduced between two adjacent vertebrae of the lumbar spinal column from the anterior direction in order to replace a spinal disc, for example.

Figure 4B:
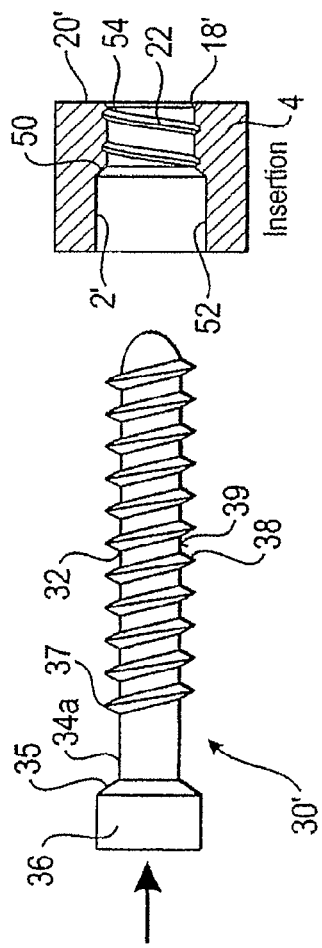
FIGS. 4A-C show in a schematic representation in three sectional views steps of inserting a fixation element having a clearance groove into a device body according to a second embodiment.
Figure 4A:
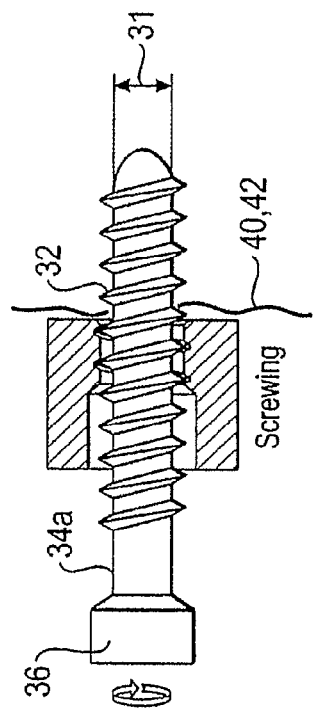
Figure 4C:
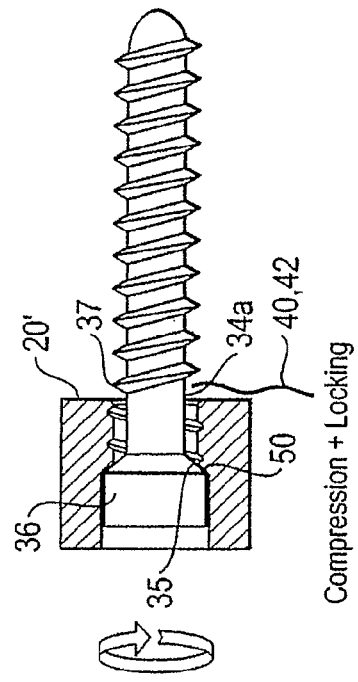

Once the cage 1 is appropriately positioned between the vertebral bodies 40, 42, bone screws 30a-c are inserted in respective bores 2a-c and screwed into end plates of the vertebral bodies 40, 42 (FIG. 3B). For explanation purposes, a simplified construction of the bores 2' and the corresponding bone screws 30' is shown in the embodiment of FIGS. 4A-C. Like numerals denote the same or similar components in the figures.

The bone screw 30' according to this embodiment (see FIG. 4A) is composed of substantially three sections: a head section 36, a first (threaded) shaft section which defines a bone thread, and a second shaft section including a clearance groove 34a. The first shaft section has an external bone thread 32 which is designed to be drilled and cut into the bone material of the adjacent end plates of the vertebral bodies 40, 42. The bone thread is formed by helical grooves 39 and helical projections 38.

The second shaft section has a clearance groove 34a that extends from a thread runout portion of the external thread towards the head section 36. The second shaft portion has a diameter, which in this embodiment is substantially the same as a core diameter 31 of the threaded portion 32, i.e., a diameter as measured with regard to the helical grooves of the external thread. In other words, the diameter of the clearance groove 34a is smaller than that of the helical projections 38 which form the thread 32 (outer diameter).

The bone screw is first inserted into the bore 2' formed in front wall 4 which has the internal thread portion 22 and a cylindrical guiding portion 52. The cylindrical guiding portion 52 is arranged to accommodate the head section 36 of the bone screw, wherein respective diameters are substantially the same in order to provide suitable guidance. Moreover, the diameter of the guiding portion 52 is larger than that of the internal thread portion 22, wherein a transition between both portions is represented by a conical stop 50, which may be engaged by a corresponding conical catch 35 formed on the head section 36 of the bone screw 30' when a state of compression is reached (see FIG. 4C).

The external bone thread 32 of the bone screw and the internal thread 22 of the bore are adapted to engage with each other. Hence, the bone screw may be screwed through the internal thread 22 (see FIG. 4B). A longitudinal length of the clearance groove 34 is substantially the same as that of the internal thread 22. More precisely, this length of the clearance groove is substantially the same as the distance between the stop 50 and the opening 18' towards the end face 20' of the front wall 4 of the cage 1. As a consequence, the thread portions 22, 32 disengage when the catch 35 abuts on the stop 50.

Further screwing leads to a compression of the cage 1 against the end plate of the vertebral body 40, 42. However, further screwing also leads to a misorientation of the helical projection 37 at the thread runout with respect to the thread inlet 54 (i.e., the groove of the internal thread which enters the opening 18') of the internal thread 22. Thus, the helical projection 37 of the external thread 32 at the thread runout abuts on the end face 20' upon further screwing (rotation of the bone screw 30').

FIGS. 5A-C show in a similarly simplified construction an alternative embodiment of the present disclosure. Same numerals denote the same or like components. In this embodiment, the head section 36 of the bone screw 30" is considerably shortened as compared with the previous second embodiment. The resulting deficiency in stably guiding the bone screw upon insertion is compensated by the feature of the clearance groove 34b, which in this embodiment has an increased thickness as compared with the core diameter 31 of the thread portion 32.

However, the diameter of the clearance groove 34b is smaller than the outer diameter due to the helical projection of the thread portion 32, such that the clearance groove may pass the internal thread portion of the bore 2". Thereby, the clearance groove 34b is in close contact to corresponding projections (not shown in detail) of the internal thread portion of the bore in order to carry out the tight guiding function for the bone screw. In other words, the internal thread portion 22 simultaneously serves as the guiding portion 52b. Numeral 52a (see FIG. 5A) merely denotes a seat for the shortened head section 36.

FIGS. 6A-C show the corresponding construction of the bone screw mechanism with regard to the first embodiment illustrated in FIGS. 1 to 3. The same numerals denote the same or like components as in the other embodiments. Shown are the steps of inserting the bone screw as shown by arrow 59 in FIG. 6A, screwing the bone screw 30a-c through the internal thread portion of the bores 2a-c as shown by arrow 60 in FIG. 6B, and further rotating the bone screw to lock the same as detailed above with respect to FIGS. 4A-C as shown by arrow 61 in FIG. 6C. Also illustrated are the resulting forces $F_1$, $F_2$ acting on the head section 36 via catch 35 and the first shaft section of the bone screw 30a-c via the external thread portion (see FIG. 6C).

Figure 7A:
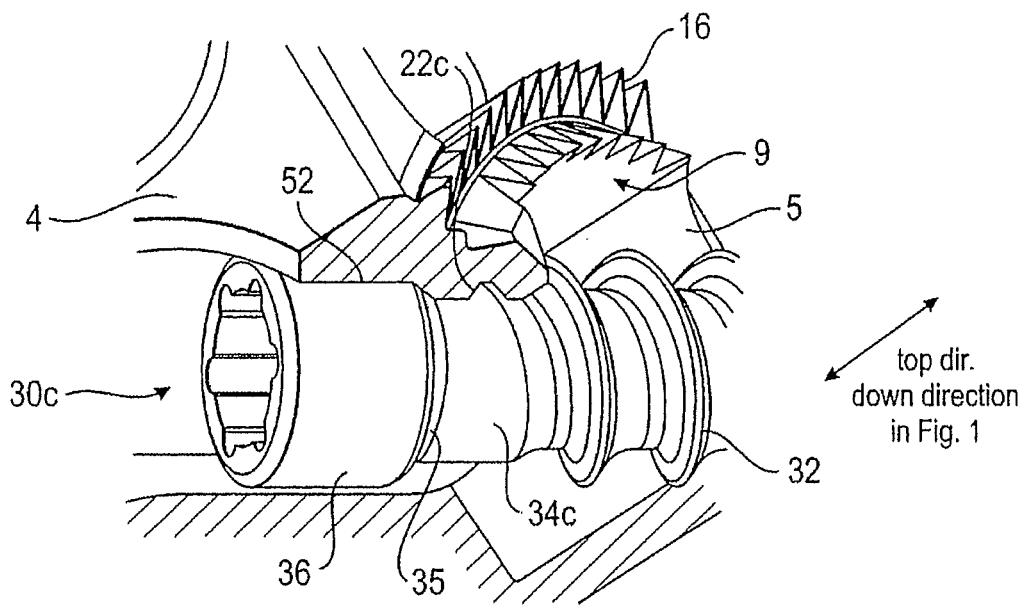
FIG. 7A shows a partially enlarged perspective exploded view of the fixation element being inserted into the bore according to the first embodiment, wherein a state of compression prior to locking is achieved.

FIGS. 7A, 7B, 8A and 8B illustrate the operation of locking or securing the intervertebral implant device 100 according to the first embodiment. In this specific embodiment a hexagon head bone screw is employed and a hexagon wrench key is applied to screw the bone screw 30c shown FIGS. 7A and 8A. FIG. 7A shows a state in which the catch 35 abuts on the stop 50 and the clearance groove 34c extends throughout the internal thread portion 22c of the bore 2c within front wall 4.

Hence, compression starts upon further screwing.

Figure 7B:
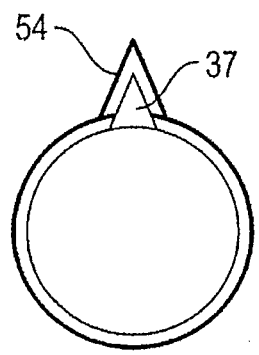
FIG. 7B shows a schematic view of the relative orientations of the thread runout of the external thread of the fixation element and the thread inlet of the internal thread of the bore of the device body as present in the state shown in FIG. 7A.
Figure 8A:
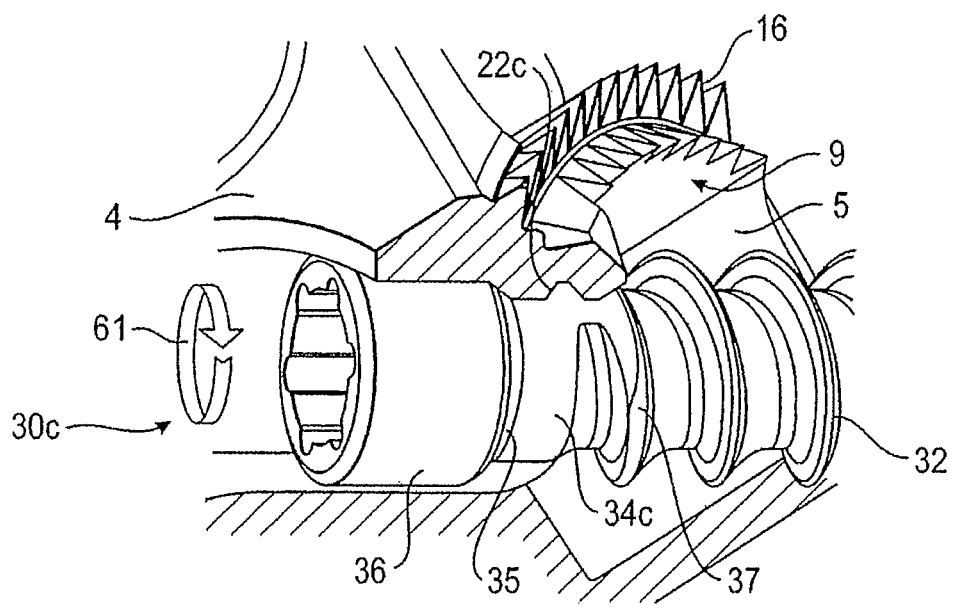
FIG. 8A shows a partially enlarged perspective exploded view of the fixation element being inserted into the bore according to the first embodiment, in a state after locking, i.e. further rotation by 90-270 degrees.
Figure 8B:
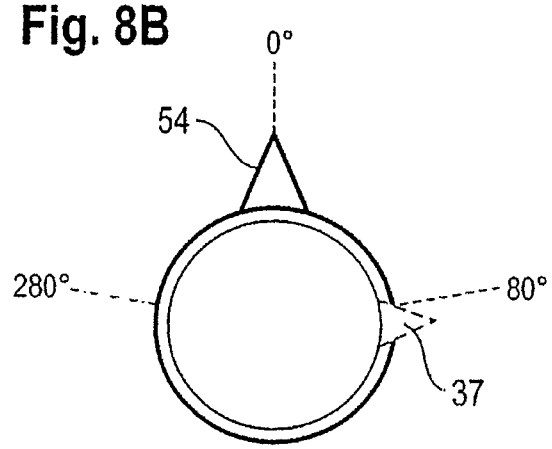
FIG. 8B shows a schematic view of the relative orientations of the thread runout of the external thread of the fixation element and the thread inlet of the internal thread of the bore of the device body with a corresponding misorientation of the thread runout versus the thread inlet resulting from the locking rotation shown in the state of FIG. 8A.

Simultaneously with further compression, further rotation 61 of the screw 30c by, e.g., 85 degrees misorients the helical projection 37 at the thread runout of the external thread portion 32 with respect to the thread inlet 54 (not visible in FIGS. 7 and 8 due to the sectional view) in the opening 22c of bore 2c. The orientation is shown in FIGS. 7B and 8B. Upon loosening of the bone screw, any force acting on the bone screw 30c to screw it out would result in an increasing abutment of the projection 37 on the end face 20c of the front wall as long as the thread runout fails to meet the thread inlet 54 of the bore 2c. Hence, a securing function is achieved with the present embodiment.

FIG. 9 shows an alternative embodiment. The same reference numerals denote the same or similar parts and components as shown in the previous embodiments. One difference is that the bone screw lacks a clearance groove. However, a protection or securing mechanism against fall-out of the screw is achieved by providing a second thread portion 330 to the bone screw 300, more specifically to the head section 36 thereof.

The bore 200 formed in the front wall 400 of the cage (or a plate 400 of a plate assembly, when a bone fixation plate is considered) comprises the first internal thread portion 220 and a cylindrical guiding portion 520 adjacent to the internal thread portion. In this embodiment, the second external thread portion 330 of the bone screw 300 cooperates with the internal thread portion of the head, while the first thread portion (bone thread) 32 merely cooperates with the bone material of the adjacent bones.

For this reason, the narrow opening 180 for receiving the shaft section of the bone screw is not provided with a thread.

The securing mechanism is as follows: after inserting the bone screw into the bore 200 of the front wall 400 of the cage, or the plate, the second thread potion (head thread) 330 is screwed through the internal thread 220 of the bore 200. AS the thread length L1 of the head thread is the same as the length of the cylindrical guiding portion 520, the external thread 330 leaves or disengages from the internal thread 220 just when the catch 35 abuts on the stop 50.

Due to the cylindrical symmetry of the guiding portion 520, the bone screw is now freely rotatable within the bore. Hence, further compression of the catch against the stop is achieved, when the bone thread is further screwed into the adjacent bone material more deeply by for example 80 or 90 degrees to 270 or 280 degrees. The helical projection 37 at the thread runout of the head thread 330 is thereby misoriented relative to the thread inlet of the internal thread 220 within the bore 200. Consequently, the projection 37 abuts on a corresponding end face 201 within the bore at a transition between internal thread 220 and the cylindrical guiding portion 520.

As a result, the screw cannot easily fall out of the cage or plate even if it is loosened in the bone material. Rather, the head section will securely be kept within the cylindrical guiding portion 520.

It is to be understood that the present disclosure shall not be limited by detailed features as explained herein. Rather, it is within the scope of the invention to apply various modifications to the embodiments described above. For example, the bone screw may be screwed into the bone material by mechanisms and tools than hexagon head screws, which are well known in the art. Also, as an example, the materials employed for the cage and the screw may be chosen according to the specific needs.

Still further, although the embodiments employing three bores for accommodating three bone screws have been found and described as providing an optimized design with regard to stress and torsion distribution, other designs employing two, four or more bore and bone screws can be employed as well. Also, the invention is not limited to the specific arrangement of inner and outer side walls of the cage as shown in the present embodiments. In particular, the invention encompasses applications regarding bone plates or similar bone fixation devices.

What is claimed is:

1. A fixation device for bones comprising:
   a bone screw; and
   a member configured to be an intervertebral implant to be fixed to one or more bones and which has at least one bore for receiving the bone screw for insertion through the at least one bore into the bone, wherein the at least one bore comprises an internal thread;
   wherein the bone screw comprises:
      a first shaft section provided with an external thread configured to cooperate with the internal thread of the at least one bore;
      a head; and
      a second shaft section comprising a clearance groove extending between the head and the external thread of the first shaft section, wherein the head has a diameter larger than a diameter of the second shaft section to provide a catch configured to engage with a stop formed in the at least one bore;
   wherein when the catch is engaged with the stop, the external thread of the first shaft section and the internal thread of the bore are entirely disengaged.

2. The fixation device according to claim 1, wherein the second shaft section of the bone screw has an outer diameter smaller than the inner diameter of the internal thread of the at least one bore.

3. The fixation device according to claim 1, wherein the second shaft section of the bone screw has a length substantially equal to a length of the portion of the at least one bore with the internal thread.

4. The fixation device according to claim 1, wherein:
   the external thread of the first shaft section comprises a helical projection;
   a thread runout is provided at a transition between the first shaft section and the second shaft section; and
   the helical projection provided at the thread runout is configured to abut on an end face of the device body surrounding an opening of the at least one bore, when the catch of the head abuts on the stop formed within the at least one bore.

5. The fixation device according to claim 1, wherein the second shaft section has an outer diameter smaller than an outer diameter of the first shaft section.

6. The fixation device according to claim 5, wherein the second shaft section has an outer diameter equal to or larger than a diameter of a core portion of the first shaft section.

7. The fixation device according to claim 6, wherein the outer diameter of the second shaft section and the diameter of the core portion of the first shaft section are equal.

8. The fixation device according to claim 1, wherein the second shaft section is non-threaded and has a substantially cylindrical shape.

9. The fixation device according to claim 1, wherein the at least one bore further has a cylindrical guiding portion extending adjacent to the stop and has a larger diameter than a diameter of the internal thread of the at least one bore in order to receive the head of the bone screw.

10. The fixation device according to claim 1, wherein the member has three bores associated with three bone screws.

11. The fixation device according to claim 1, wherein the member is configured as an anterior lumbar interbody fusion device.

12. The fixation device according to claim 1, wherein the member comprises a device body having an upper face and a lower face for engaging with end plates of an upper vertebral body and a lower vertebral body, respectively, and a side wall including the at least one bore.

13. The fixation device according to claim 12, wherein the member has three bores associated with three bone screws, and wherein the three bores are arranged in a front wall forming part of the side wall of the device body.

14. The fixation device according to claim 13, wherein the front wall is further connected to a back wall via two first arc-shaped vertical inner walls.

15. The fixation device according to claim 14, wherein a left side wall and a right side wall forming part of the side wall are each connected with the back wall via two second arc-shaped inner walls.

16. The fixation device according to claim 15, wherein each one of the three bores opens toward a separate inner space of the device body, and wherein each of the inner spaces is configured to be open towards the end plates of the adjacent vertebral bodies and defined by one of:
   (a) a space between the two first arc-shaped inner walls;
   (b) a space between one of the two first arc-shaped inner walls and a left one of the two second arc-shaped inner walls; and (c) a space between the other of the two first arc-shaped inner walls and a right one of the two second arc-shaped inner walls.

17. The fixation device according to claim 12, wherein the upper and lower faces of the device body are provided with small teeth configured to penetrate into the end plates of the adjacent vertebral bodies upon compression by the bone screw being screwed into the adjacent vertebral bodies.

18. The fixation device according to claim 13, wherein the upper face, the lower face, and the side wall define an inner space of the device body, and wherein the at least one bore opens into the inner space.

19. A method of implanting an intervertebral implant device between two adjacent vertebral bodies, comprising:
   inserting a device body between the two adjacent vertebral bodies, the device body having an upper face and a lower face for engaging with an end plate of an upper and a lower vertebral body, respectively, a side wall, and at least one bore formed in the side wall for receiving a bone screw, and the at least one bore further comprising an internal thread;
   attaching the bone screw to the at least one bore, the bone screw having a first shaft section comprising an external thread configured to cooperate with the internal thread of the at least one bore, a head, and a second shaft section comprising a clearance groove extending between the head and the external thread of the first shaft section, wherein the head has a diameter larger than a diameter of the second shaft section to provide a catch configured to engage with a stop formed in the at least one bore;
   screwing the bone screw such that the external thread is screwed through the internal thread until (a) the catch abuts the stop, and (b) the external thread and the internal thread entirely disengage from each other due to the clearance groove, in order to compress the device body towards the adjacent vertical bodies; and
   applying a further screwing movement of the bone screw to protect the bone screw against loosening.

20. A method of attaching a fixation device to a bone, the fixation device comprising a member configured to be fixed to one or more bones and has at least one bore for receiving a bone screw for insertion through the at least one bore into the bone, wherein the at least one bore comprises an internal thread, the bone screw having a first shaft section provided with an external thread configured to cooperate with the internal thread of the at least one bore, a head, and a second shaft section comprising a clearance groove extending between the head and the external thread of the first shaft section, wherein the head has a diameter larger than a diameter of the second shaft section to provide a catch configured to engage with a stop formed in the at least one bore, and wherein the member is an intervertebral implant comprising a device body having an upper face and a lower face for engaging with end plates of an upper and lower vertebral bodies, respectively, and a side wall including the at least one bore, the method comprising:
   inserting the bone screw through the at least one bore by screwing the external thread of the first shaft section in the internal thread of the at least one bore;
   screwing the bone screw into a vertebrae to a first position until the catch abuts the stop, wherein the external thread entirely disengages from the internal thread;
   screwing the bone screw further into the vertebrae to a second position;
   wherein engagement of the external thread with the internal thread is prevented when unscrewing the bone screw from the second position toward the first position.

21. The method according to claim 20, further comprising:
   inserting a second bone screw through a second bore of the member by screwing an external thread of a first shaft section of the second bone screw in an internal thread of the second bore;
   screwing the second bone screw into an adjacent vertebrae to a first position until a catch of the second bone screw abuts a stop of the second bore, wherein the external thread of the second bone screw disengages from the internal thread of the second bore;
   screwing the second bone screw further into the adjacent vertebrae to a second position;
   wherein engagement of the external thread of the second bone screw with the internal thread of the second bore is prevented when unscrewing the second bone screw from the second position toward the first position.

* * * * *

UNITED STATES PATENT AND TRADEMARK OFFICE
CERTIFICATE OF CORRECTION

PATENT NO. : 8,834,570 B2  
APPLICATION NO. : 13/613584  
DATED : September 16, 2014  
INVENTOR(S) : Lutz Biedermann et al.

Page 1 of 1

It is certified that error appears in the above-identified patent and that said Letters Patent is hereby corrected as shown below:

On the Title Page

Item (75) Inventors, line 1   Delete "Villingen (DE)"  
Insert -- VS-Villingen (DE) --

In the Specification

Column 2, line 53   Delete "aspect. I.e.,"  
Insert -- aspect, i.e., --

Column 3, line 59   Delete "a"  
Insert -- an --

Column 7, line 5   Delete "potion"  
Insert -- portion --

Column 7, line 31   After "tools"  
Insert -- other --

In the Claims

Column 9, line 9, Claim 18   Delete "claim 13,"  
Insert -- claim 12, --

Signed and Sealed this  
Twenty-first Day of July, 2015

Michelle K. Lee  
*Director of the United States Patent and Trademark Office*